(12) United States Patent
Hokamura (10) Patent No.: US 8,342,019 B2
(45) Date of Patent: Jan. 1, 2013

(54) EXHAUST GAS ANALYZER AND PROBE UNIT

(75) Inventor: Shigeyuki Hokamura, Kyoto (JP)

(73) Assignee: Horiba, Ltd., Kyoto, Kyoto (JP)

( * ) Notice: Subject to any disclaimer, the term of this patent is extended or adjusted under 35 U.S.C. 154(b) by 297 days.

(21) Appl. No.: 12/788,935

(22) Filed: May 27, 2010

(65) Prior Publication Data

US 2010/0300175 A1  Dec. 2, 2010

(30) Foreign Application Priority Data

May 29, 2009 (JP) .................................. 2009-131435
May 29, 2009 (JP) .................................. 2009-131436
May 29, 2009 (JP) .................................. 2009-131437

(51) Int. Cl.
  *G01D 11/24*  (2006.01)

(52) U.S. Cl. ....... 73/431; 73/24.06; 73/25.05; 73/31.05; 73/866.5

(58) Field of Classification Search .................... 73/1.02, 73/23.2, 24.06, 25.05, 30.04, 31.05, 431, 73/866.5

See application file for complete search history.

(56) References Cited

U.S. PATENT DOCUMENTS

| | | |
|---|---|---|
| 5,284,054 A | 2/1994 | Loebach |
| 7,370,512 B2 * | 5/2008 | Nakashima et al. ........... 73/23.2 |
| 2009/0165575 A1 * | 7/2009 | Roucis ........................ 73/863.23 |
| 2010/0170483 A1 * | 7/2010 | Wienand et al. ......... 123/568.12 |
| 2010/0175865 A1 * | 7/2010 | Murphy ......................... 165/200 |

FOREIGN PATENT DOCUMENTS

| | | |
|---|---|---|
| JP | 63085352 | 4/1988 |
| JP | 01146152 | 10/1989 |
| JP | 02024376 | 2/1990 |
| JP | 20010045503 | 1/2001 |
| JP | 2006184266 A | 7/2006 |
| JP | 2006234568 | 9/2006 |
| JP | 200942165A A | 2/2009 |

* cited by examiner

*Primary Examiner* — David Rogers
(74) *Attorney, Agent, or Firm* — Brooks Kushman P.C.

(57) ABSTRACT

A probe unit includes a gas sensor having multiple gas introduction bores for introducing a gas into an inside of the gas sensor, and a sensor holder inside of which the gas sensor is held and that is arranged inside of a duct so as to introduce an exhaust gas flowing in the duct into the gas sensor. A calibration gas flow channel is arranged in the sensor holder and has an opening at an inner surface of a side wall, surrounding the gas introduction bores of the gas sensor, of the sensor holder so as to supply a calibration gas to the gas sensor. A guide groove is arranged continuous to the opening of the calibration gas flow channel and arranged on the inner surface of the side wall along an arranging direction of the multiple gas introduction bores to face the multiple gas introduction bores.

6 Claims, 6 Drawing Sheets

EXHAUST GAS ANALYZER AND PROBE UNIT

CROSS-REFERENCE TO RELATED APPLICATIONS

This application claims the benefit of JP 2009-131437, filed May 29, 2009; JP 2009-131436, filed May 29, 2009; and JP 2009-131435, filed May 29, 2009. The disclosures of which are incorporated in their entirety by reference herein.

TECHNICAL FIELD

This invention relates to an exhaust gas analyzer and a probe unit used for the exhaust gas analyzer mounted on an exhaust pipe of combustion equipment such as, for example, an engine, a boiler, a waste combustion furnace, or an industrial furnace to analyze a predetermined component contained in an exhaust gas flowing in a duct in the exhaust pipe.

BACKGROUND

Conventionally, as shown in Japan Patent Laid-open number 2006-184266 and Japan Patent Laid-open number 2009-42165, there is an exhaust gas analyzer for detecting and analyzing a predetermined component such as oxygen or nitrogen oxide contained in an exhaust gas in a duct that has an arrangement that a probe unit is directly inserted into a duct and mounted on the duct and the exhaust gas is sampled by the probe unit and a predetermined component such as, for example, oxygen or nitrogen oxide in the exhaust gas is detected.

Concretely the probe unit comprises a gas sensor having multiple gas introduction bores to introduce the gas into inside of the gas sensor and a sensor holder inside of which the gas sensor is held and that is arranged to be inserted in the duct so as to introduce the exhaust gas flowing in the duct into the gas sensor. A single calibration gas flow channel to supply a calibration gas to the gas sensor is formed in the sensor holder, and the calibration gas flow channel opens on an inner surface of a side wall surrounding the gas introduction bores of the gas sensor. With this arrangement, the calibration gas is supplied to the gas sensor by spraying the calibration gas over the gas introduction bores from the calibration gas flow channel so that the gas sensor is corrected.

However, since the calibration gas is supplied to the multiple gas introduction bores through a single calibration gas flow channel, there is a problem that it fails to sufficiently supply the calibration gas to inside of the gas sensor through the gas introduction bores. Especially, since the probe unit is arranged to be inserted inside of the duct, in case that the pressure in the duct is a negative pressure, there is a problem that it fails to sufficiently supply the calibration gas to the gas sensor because the probe unit is influenced by the pressure in the duct such that the calibration gas is pulled into inside of the duct prior to flowing into the gas introduction bores. Under this situation, in order to try to supply the sufficient calibration gas to inside of the gas sensor, there is also another problem that a consumption amount of the calibration gas increases.

In addition, it can be conceived that an opening of the calibration gas flow channel is arranged to face to one of the multiple gas introduction bores at a time of assembling the probe unit or the calibration gas flow channel is arranged to branch so as to face an opening of each branched channel to the gas introduction bore respectively in order to make it possible to sufficiently supply the calibration gas to inside of the gas sensor through multiple gas introduction bores, however, it is difficult to make the opening of the calibration gas flow channel face to the gas introduction bore in view of an assembling accuracy. Furthermore, with an arrangement where the calibration gas flow channel is branched, an arrangement of the sensor holder becomes complicated and jumboized, resulting in being unrealistic.

SUMMARY

The present claimed invention intends to solve all of the problems and a main object of this invention is to surely pervade a calibration gas over all of multiple gas introduction bores without increasing a consumption amount of the calibration gas with a simple and easy to assemble arrangement.

More specifically, a probe unit in accordance with this invention is characterized by comprising a gas sensor having multiple gas introduction bores to introduce a gas into inside of the gas sensor, a sensor holder inside of which the gas sensor is held and that is arranged to be inserted inside of the duct so as to introduce the exhaust gas flowing in the duct into the gas sensor, a calibration gas flow channel that is arranged in the sensor holder and that opens at an inner surface of a side wall, surrounding the gas introduction bores of the gas sensor, of the sensor holder so as to supply a calibration gas to the gas sensor, and a guide groove that is arranged continuous to the opening of the calibration gas flow channel and arranged on the inner surface of the side wall along the arranging direction of the multiple gas introduction bores to face the multiple gas introduction bores.

In accordance with this arrangement, in spite of a simple arrangement that the guide groove is arranged on the inner surface of the side wall surrounding the gas introduction bores along the arranging direction of the multiple gas introduction bores, the calibration gas supplied from the calibration gas flow channel flows along the guide groove. As a result, it is possible both to make the calibration gas difficult to be affected by a pressure in the duct and to pervade the calibration gas over all of the multiple gas introduction bores without increasing a consumption amount of the calibration gas. In addition, since the guide groove that is continuous to the opening of the calibration gas flow channel is arranged along the arranging direction of the multiple gas introduction bores, it is possible to introduce the calibration gas to the gas introduction bores irrespective of a positional relationship between the opening of the calibration gas flow channel and the gas introduction bores, which makes it possible to mount the gas sensor on the sensor holder with ease.

In order to mount the gas sensor on the sensor holder further more easily irrespective of a positional relationship between the opening of the calibration gas flow channel and the gas introduction bores, it is preferable that the guide groove is formed to surround an entire circumference of the inner surface of the side wall.

However, with an arrangement that the guide groove is just arranged as mentioned above, there might be a case that the calibration gas fails to reach the gas introduction bores depending on the pressure in the duct. In order to solve this problem it is preferable that the calibration gas flow channel supplies the calibration gas to the gas sensor by speeding up a flow rate of the calibration gas by narrowing a flow channel on the opening side of the calibration gas flow channel. In addition, with this arrangement, since it is possible to obtain a sufficient flow rate with a small amount of the calibration gas, a consumption amount of the calibration gas can be reduced.

In addition, an exhaust gas analyzer in accordance with this invention uses the above-mentioned probe unit that takes a sample of an exhaust gas flowing in a duct and that is characterized by comprising a gas sensor having multiple gas introduction bores to introduce a gas into inside of the gas sensor, a sensor holder inside of which the gas sensor is held and that is arranged to be inserted inside of the duct so as to introduce the exhaust gas flowing in the duct into the gas sensor, a calibration gas flow channel that is arranged in the sensor holder and that opens on an inner surface of a side wall, surrounding the gas introduction bores of the gas sensor, of the sensor holder so as to supply a calibration gas to the gas sensor, and a guide groove that is arranged continuous to the opening of the calibration gas flow channel and on the inner surface of the side wall along the arranging direction of the multiple gas introduction bores to face the multiple gas introduction bores.

Furthermore, a probe unit that is free from a thermal influence on peripheral devices with securing safety for an operator and that is free from a problem due to a pressure influence in the duct is a probe unit that takes a sample of an exhaust gas flowing in a duct and is characterized by comprising a sensor holder inside of which a gas sensor is held and that is arranged to be inserted in the duct to introduce the exhaust gas flowing in the duct into the gas sensor, a cooling air flow channel that is arranged in the sensor holder to supply a cooling air to the gas sensor and a cooling air exhaust port of which is arranged outside of the duct, an exhaust pipe whose one end is connected to the cooling air exhaust port and the other end of which is in communication with the duct, and a check valve that is arranged in the exhaust pipe to allow a circulation only from the cooling air exhaust port side to the duct side.

With this arrangement, since the exhaust pipe is connected to the cooling air exhaust port and the exhaust pipe is in communication with the duct, the heated cooling air will not be discharged outside of the duct. As a result, it is possible to secure security for the operator and to eliminate a thermal influence on the peripheral devices. In addition, since the check valve is arranged in the exhaust pipe, it is possible to prevent the exhaust gas in the duct from flowing into the cooling air flow channel in a state that the duct is in a pressurized state, thereby eliminating a problem due to a pressure influence in the duct.

It is preferable that the sensor holder is of a double pipe structure comprising an inner pipe and an outer pipe, the gas sensor is held in the inner pipe, an outward channel of the cooling air flow channel is formed in the inner pipe, a homeward channel of the cooling air flow channel is formed in a space formed by the inner pipe and the outer pipe, and a through bore that communicates the outward channel with the homeward channel is formed on a distal end side of the inner pipe in the axial direction. With this arrangement, since the through bore is formed on the distal end side of the inner pipe in the axial direction, since the cooling air touches entire part where the gas sensor is housed in the inner pipe, it is possible to sufficiently cool the gas sensor. In addition, since the cooling air flows in the space between the inner pipe and the outer pipe, it is possible to produce insulation effect between the exhaust gas in the duct and the gas sensor, thereby enabling to further cool the gas sensor.

Furthermore, the exhaust gas analyzer in accordance with this invention uses the above-mentioned probe unit that is characterized by comprising a sensor holder inside of which a gas sensor is held and that is arranged to be inserted in the duct to introduce the exhaust gas flowing in the duct into the gas sensor, a cooling air flow channel that is arranged in the sensor holder to supply a cooling air to the gas sensor and a cooling air exhaust port of which is arranged outside of the duct, an exhaust pipe whose one end is connected to the cooling air exhaust port and the other end of which is in communication with the duct, and a check valve that is arranged in the exhaust pipe to allow a circulation only from the cooling air exhaust port side to the duct side.

A probe unit that makes it possible not only to check the sensitivity deterioration of the gas sensor without dismounting the probe unit from the duct and to conduct a comparison test with the gas sensor in the probe unit but also to eliminate clogging of a filter so as to elongate a lifetime of the filter is a probe unit that takes a sample of an exhaust gas flowing in a duct and that is characterized by comprising a sensor holder inside of which a gas sensor is held and that is arranged to be inserted inside of the duct so as to introduce the exhaust gas flowing in the duct into the gas sensor through a filter, and a cleaning and measuring gas flow channel that is arranged in the sensor holder to supply a cleaning gas to the filter from the gas sensor side to the duct side at a time of cleaning and to introduce a part of the exhaust gas passing the filter into a measuring device that is different from the gas sensor at a time of measurement.

In accordance with this arrangement, at a time of cleaning the filter, if the cleaning gas flows to pass the filter from the gas sensor side to the duct side by the use of the cleaning and measuring gas flow channel, it is possible to eliminate clogging of the filter so that a lifetime of the filter is elongated and a running cost can be reduced. In addition, at a time of measurement, since the exhaust gas passing the filter can be introduced to a measuring device that is different from the gas sensor by the use of the cleaning and measuring flow channel, the sensitivity deterioration of the gas sensor can be checked and a comparison test can be also conducted without dismounting the probe unit from the duct by comparing a measurement result of the measuring device and the measurement result obtained by the gas sensor. Furthermore, multiple items of the exhaust gas can be analyzed if a measuring device that can measure a measurement item that is different from the measurement item of the gas sensor is connected.

In order to check the sealing effect in the sensor holder ant to check the sensitivity deterioration more accurately, it is preferable that the probe unit further comprises a calibration gas flow channel that is arranged in the sensor holder to supply the calibration gas to the gas sensor and the cleaning and measuring gas flow channel introduces a part of the calibration gas supplied from the calibration gas flow channel into the measuring device at a time of calibration.

In addition, the exhaust gas analyzer in accordance with this invention uses the above-mentioned probe unit, which takes a sample of the exhaust gas flowing in the duct, and that is characterized by comprising a sensor holder inside of which a gas sensor is held and that is arranged to be inserted in the duct to introduce the exhaust gas flowing in the duct into the sensor holder through a filter, and a cleaning and measuring gas flow channel that is arranged in the sensor holder to supply a cleaning gas to the filter from the gas sensor side to the duct side at a time of cleansing and to introduce a part of the exhaust gas passing the filter into a measuring device that is different from the gas sensor at a time of measurement.

In accordance with this invention of the above-mentioned arrangement, it is possible to surely pervade the calibration gas over all of the gas introduction bores without increasing a consumption amount of the calibration gas with a simple and easy to assemble arrangement.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

One embodiment of an exhaust gas analyzer in accordance with this invention will be explained with reference to drawings.

<Configuration>

The exhaust gas analyzer 100 in accordance with this embodiment is of a direct insert type that analyzes a predetermined component (for example, $NO_x$, $SO_x$, $CO_2$, CO or the like) contained in an exhaust gas G flowing in a duct of an exhaust pipe H connected to a boiler such as a lime fuel boiler or a heavy oil boiler or an internal combustion of a gas engine or an engine for marine. A result @of analysis (for example, a concentration of a predetermined component) obtained by the exhaust gas analyzer 100 is used for controlling denitration or desulfurization.

Figure 1:
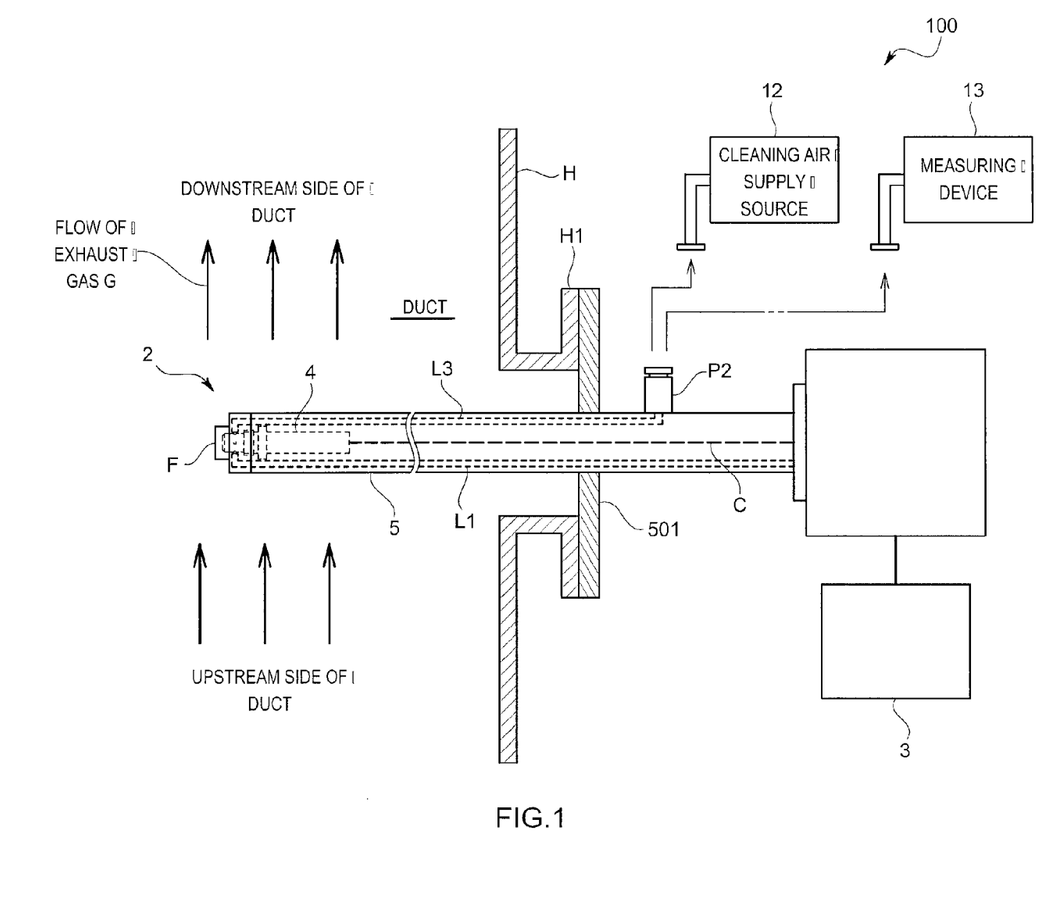
FIG. 1 is a pattern diagram mainly showing a calibration gas flow channel and a cleaning and measuring gas flow channel in an exhaust gas analyzer in accordance with one embodiment of this invention.
Figure 2:
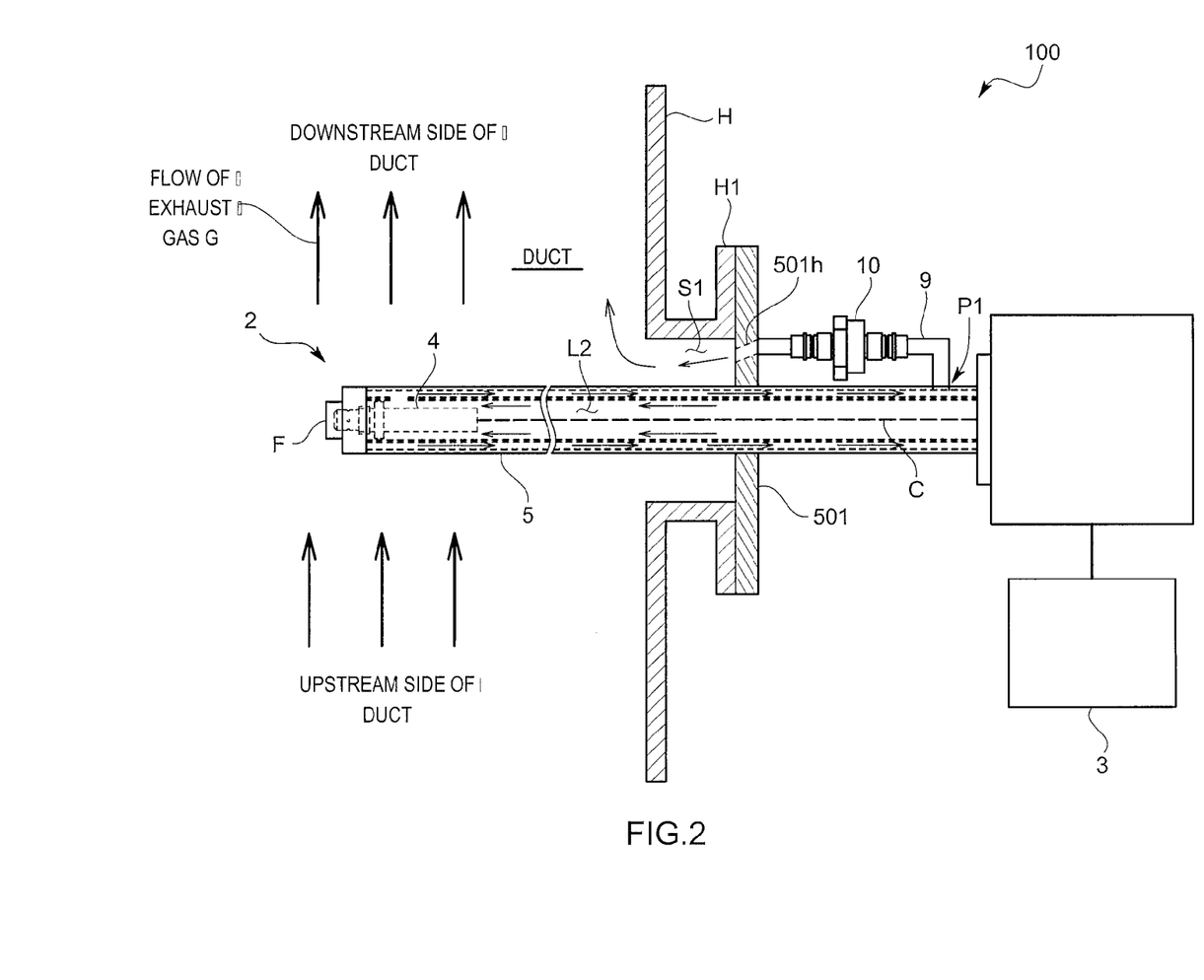
FIG. 2 is a pattern diagram mainly showing a cooling air flow channel in the exhaust gas analyzer in accordance with this embodiment.

Concretely, as shown in FIG. 1 and FIG. 2, the exhaust gas analyzer 100 comprises a probe unit 2 whose distal end part is inserted in the duct by being fixed to an exhaust pipe H and inside of which a gas sensor 4 for detecting a predetermined component is arranged and a control unit 3 to receive a detected signal from the probe unit 2 and to analyze the predetermined component contained in the exhaust gas G continuously with fast response. The control unit 3 comprises a computation part and a display part (not shown in drawings), and the probe unit 2 is connected to the control unit 3 through a cable.

Figure 3:
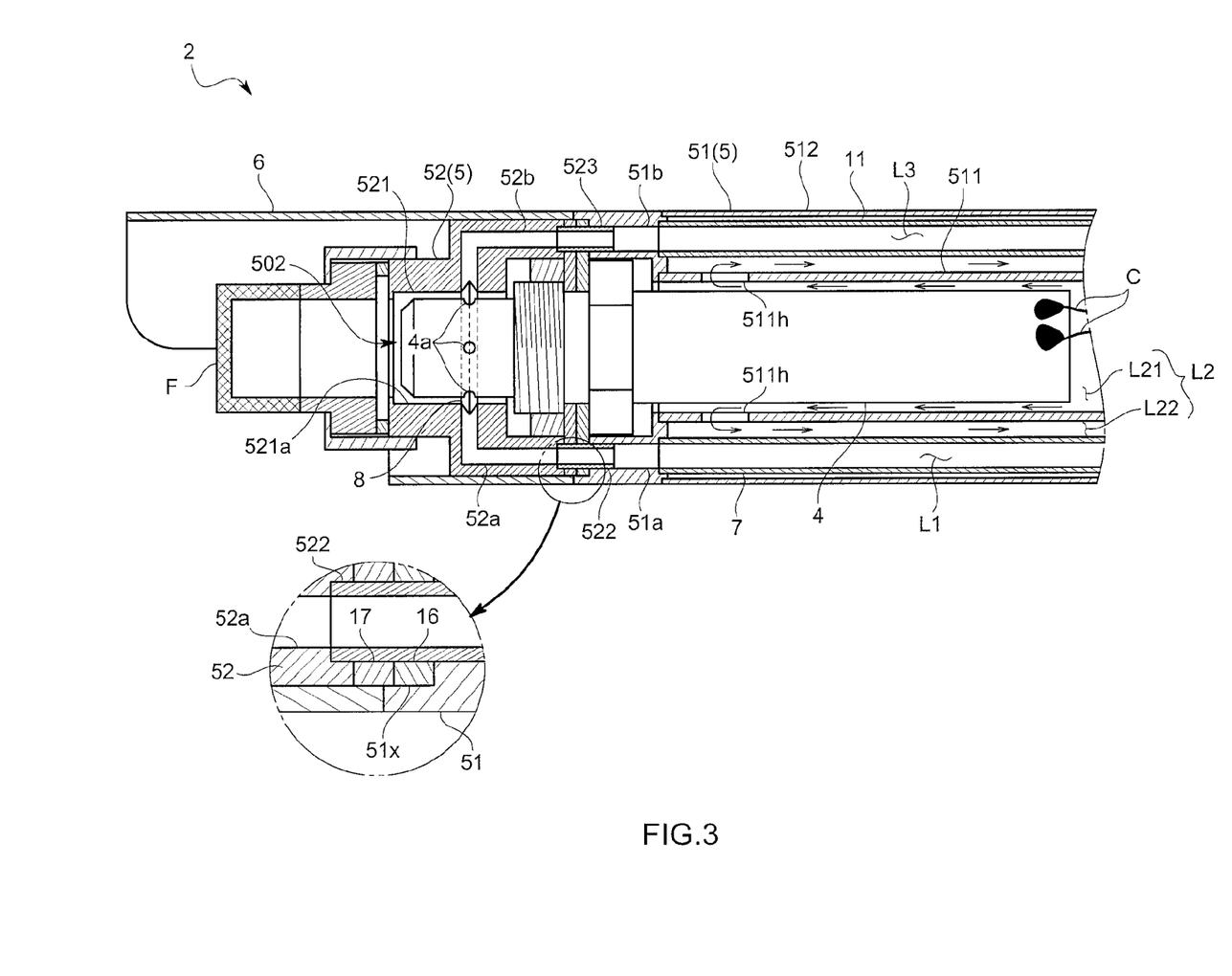
FIG. 3 is a cross-sectional view in an axial direction showing a distal end part of a probe unit of this embodiment.

As shown in FIG. 1 and FIG. 2, the probe unit 2 takes a sample of the exhaust gas G flowing in the duct and detects the predetermined component contained in the sampled exhaust gas G, and comprises, as shown in FIG. 3, the gas sensor 4 having multiple gas introduction bores 4a to introduce a gas into inside of the gas sensor 4 and a sensor holder 5 inside of which the gas sensor 4 is held and that is arranged to be inserted inside of the duct so as to introduce the exhaust gas G flowing in the duct into the gas sensor 4.

The gas sensor 4 comprises a sensor element of a high temperature operation type using a plate-shape or a bar-shaped oxygen ion conductive solid electrolyte, a heater to apply heat to the sensor element and a sensor case of generally cylindrical shape to house the sensor element and the heater.

As shown in FIG. 3, the multiple gas introduction bores 4a to introduce the gas into the sensor element are formed on a distal end side of the sensor case at a predetermined interval (equally 90 degrees in this embodiment) along a circumferential direction of the sensor case. In addition, a pair of electrodes are arranged for the sensor element so that the concentration of the predetermined component in the exhaust gas G can be detected by measuring a current generated resulting from a potential difference between both electrodes. A lead wire C to output the current generated by the sensor element to outside is, for example, soldered at a proximal end part of the sensor case (refer to FIG. 3).

The sensor holder 5 is generally in a cylindrical shape and at least an external diameter of a part that is inserted into the exhaust pipe H becomes constant. In addition, a flange part 501 to screw and fix the sensor holder 5 to a mounting part H1 arranged for the exhaust pipe H is formed at a proximal end part of the sensor holder 5 (refer to FIG. 1). As shown in FIG. 3, an opening part 502 to introduce the exhaust gas G into inside of the sensor holder 5 is formed at a distal end part of the sensor holder 5. In addition, a filter F for dust proof to remove dust in the exhaust gas G to be sampled in the sensor holder 5 is arranged at the opening part 502. A numerical code 6 in FIG. 3 is a surrounding plate that extends from the distal end part of the sensor holder 5 and surrounds the opening part 502 and a space in front of the filter F at least from the upstream side of the duct.

The filter F is generally in a shape of a cylinder having a bottom wall in order to enlarge its surface area as much as possible and mounted on the sensor holder 5 so as to cover the opening part 502 with its bottom wall locating on the distal end side. With this arrangement, it is possible to enlarge the surface area of the filter F as much as possible and to prevent imperviousness of the exhaust gas G due to clogging of the filter F. In addition, it is also possible to alleviate a pressure influence due to clocking of the filter F at a time of calibration.

Furthermore, as shown in FIG. 3, the sensor holder 5 has a double pipe element 51 having a double pipe structure comprising an inner pipe 511 and an outer pipe 512 and a fixing element 52 to house and fix the gas sensor 4 on a distal end side of an inside of the double pipe element 51. A proximal end part of the gas sensor 4 is housed in the inner pipe 511 of the double pipe element 51 and a distal end part of the gas sensor 4 is housed in the fixing element 52. Concretely, the fixing element 52 has a hollow part 521 to house the distal end part (including a part where the gas introduction bores 4a are formed) of the gas sensor 4. An opening locating on a distal end side of the hollow part 521 functions as the opening part 502 of the sensor holder 5. In addition, an inner surface 521a of the hollow part 521 is formed concentrically with an outside circumferential surface, where the gas introduction bores 4a are formed, of the gas sensor 4.

<Regarding a Calibration Gas Flow Channel L1>

For the sensor holder 5 of this embodiment, as shown in FIG. 3, a calibration gas flow channel L1 for supplying a calibration gas to the gas sensor 4 is formed to open on an inner surface of a side wall of the sensor holder 5 surrounding the gas introduction bores 4a of the gas sensor 4, namely, at the inner surface 521a of the hollow part 521.

The calibration gas flow channel L1 comprises a calibration gas piping 7 arranged between the inner pipe 511 and the outer pipe 512 of the sensor holder 5 along an axial direction of the sensor holder 5, an internal flow channel 51a formed on a distal end wall of the double pipe element 51 to which the calibration gas piping 7 is connected, and an internal flow channel 52a formed inside of the fixing element 52 of the sensor holder 5. A calibration gas supply source (not shown in drawings) is connected to an outside connection port (not shown in drawings) of the calibration gas piping 7. A connection pipe 522 to connect the fixing element 52 to the internal flow channel 51*a* formed on the distal end wall of the double pipe element 51 is welded at an opening part on the piping connection side of the internal flow channel 52*a* of the fixing element 52. The calibration gas flow channel L1 is formed by fittingly inserting the connection pipe 522 into the internal flow channel 51*a* of the double pipe element 51.

The calibration flow channel L1 is so arranged that the calibration gas is supplied to the gas sensor 4 (concretely, to the gas introduction bores 4*a*) by speeding up a flow rate of the calibration gas by narrowing a flow channel on the opening side of the downstream side of the calibration gas flow channel L1. More concretely, the flow channel on the opening side of the downstream side of the calibration gas flow channel L1 is narrowed by making the internal diameter (for example, 4 mm) of the internal flow channel 52*a* formed in the fixing element 52 smaller than the internal diameter (for example, 6 mm) of the calibration gas piping 7.

<Regarding a Guide Groove 8>

The sensor holder 5 of the probe unit 2 in accordance with this embodiment, as shown in FIG. 3, has a guide groove 8 that is arranged continuously to the opening on the downstream side of the calibration gas flow channel L1 in order to pervade the calibration gas from the calibration gas flow channel L1 over the multiple gas introduction bores 4*a*.

The guide groove 8 is arranged on the inner surface 521*a* of the hollow part 521 to face the multiple gas introduction bores 4*a* along its arranging direction. Since the gas introduction bores 4*a* of this embodiment is arranged along the circumferential direction of the gas sensor 4 (concretely, a sensor case of a cylindrical shape), the guide groove 8 is also arranged along the circumferential direction. In addition, the guide groove 8 is formed to surround an entire circumference of the inner surface 521*a* of the hollow part 521 in order to make it possible to pervade the calibration gas coming out from the calibration gas flow channel L1 all over in the circumferential direction. The guide groove 8 in FIG. 2 is in a shape of a "V" character in cross-section, and may be in a channel shape or a semicircle shape in cross-section as far as the calibration gas flowing along the guide groove 8 flows toward the gas introduction bores 4*a*.

<Regarding a Cooling Air Flow Channel L2>

Furthermore, as shown in FIG. 2, the sensor holder 5 is provided with a cooling air flow channel L2 that has a cooling air exhaust port P1 outside of the duct to supply the air for cooling to the gas sensor 4, an exhaust pipe 9 whose one end is connected the cooling air exhaust port P1 and the other end of which is in communication with the duct, and a check valve 10 that is arranged on the exhaust pipe 9 to allow a circulation only from the cooling air exhaust port side to the duct side.

The cooling air flow channel L2 comprises, as shown in FIG. 3, a cooling air outward channel L21 formed in the inner pipe 511, and a cooling air homeward channel L22 formed in a space formed between the inner pipe 511 and the outer pipe 512. In this embodiment, the space in the inner pipe 511 itself forms the cooling air outward channel L21 and the space between the inner pipe 511 and the outer pipe 512 itself forms the cooling air homeward channel L22. The cooling air outward channel L21 is in communication with the cooling air homeward channel L22 through one or multiple through bores 511*h* formed on a distal end side of the inner pipe 511 in the axial direction.

A cooling air supply source (not shown in drawings) to introduce the cooling air into the inner pipe 511 is connected to a proximal end side of the inner pipe 511 in the axial direction. In addition, an opening (the cooling air exhaust port P1) on a downstream side of the cooling air homeward channel L22 is arranged on the proximal end side of the outer pipe 512 in the axial direction so as to locate outside of the duct.

As mentioned, since all of the space in the inner pipe 511 becomes the cooling air outward channel L21, it is possible to evenly expose all of the proximal end part of the gas sensor 4 housed in the inner pipe 511 to the cooling air, thereby enabling to cool the proximal end part of the gas sensor 4 effectively. In addition, since the cooling air flows in the space between the inner pipe 511 and the outer pipe 512, it is possible to produce insulation effect between the exhaust gas G in the duct and the gas sensor 4, thereby enabling to further cool the gas sensor 4.

The other end of the exhaust pipe 9 is connected to a through bore 501*h* formed on the flange part 501. The through bore 501*h* is formed on the downstream side of the duct in the flange part 501. Then in a state that the flange part 501 of the sensor holder 5 is fixed to the mounting part H1 of the exhaust pipe H, the cooling air passing the through bore 501*h* passes a gap S1 formed between the outer circumferential surface of the sensor holder 5 and an inner surface of a bore of the exhaust pipe H for inserting the sensor holder 5, and then is discharged to the downstream side of the duct from the probe unit 2. With this arrangement, the cooling air from the cooling air exhaust port P1 can be discharged into the duct without providing any processing to the exhaust pipe H constituting the duct. In addition, since the cooling air is discharged to the downstream side of the duct, it is possible to prevent an adverse effect on a measurement result due to the cooling air discharged to the duct. Furthermore, since the check valve 10 is arranged outside of the duct, it is possible to ignore a thermal influence on the check valve 10 received from the exhaust gas G.

<Regarding a Cleaning and Measuring Gas Flow Channel L3>

The sensor holder 5 further comprises, as shown in FIG. 1, a cleaning and measuring gas flow channel L3 to supply a cleaning gas for cleaning the filter F or to introduce a part of the exhaust gas G passing the filter F into a different measuring device different from the gas sensor 4.

The cleaning and measuring gas flow channel L3 comprises, as shown in FIG. 3, a cleaning and measuring gas piping (hereinafter called just as a cleaning gas piping 11) arranged in the axial direction of the sensor holder 5 between the inner pipe 511 and the outer pipe 512 of the sensor holder 5, an internal flow channel 51*b* formed in a distal end wall of the double pipe element 51 to which the cleaning gas piping 11 is connected, and an internal flow channel 52*b* formed inside of the fixing element 52 of the sensor holder 5. As shown in FIG. 1, a cleaning gas supply source 12 or a measuring device 13 that is different from the gas sensor 4 is connected to an outside connection port P2, arranged outside of the duct, of the cleaning gas piping 11. Similar to the calibration gas flow channel L1, a connection pipe 523 is welded to an opening part on a piping connection side of the internal flow channel 52*b* of the fixing element 52. The cleaning and measuring gas flow channel L3 is formed by fittingly inserting the connection pipe 523 into the internal flow channel 51*b* of the double pipe element 51. The internal flow channel 52*b* of the fixing element 52 constituting the cleaning and measuring gas flow channel L3 opens at the guide groove 8 in this embodiment, however, it is not limited to this and may open at a part avoiding the guide groove 8.

In accordance with the cleaning and measuring gas flow channel L3 having the above-mentioned arrangement, the connection port P2 of the cleaning and measuring gas flow channel L3 is connected to the cleaning gas supply source 12 at a time of cleaning the filter F. Then the cleaning gas supplied from the cleaning gas supply source 12 passes the cleaning gas piping 11 and the internal flow channels 51b, 52b and then is supplied to the hollow part 521 of the fixing element 52, and the cleaning gas supplied to the hollow part 521 flows the filter F from the gas sensor side to the duct side. When the cleaning gas flows the filter F, dust that is clogged in the filter F is removed toward the duct side.

Meanwhile, at a time of measurement (for example, at a time of comparison measurement or at a time of measuring a sensitivity of the gas sensor 4), the connection port P2 of the cleaning and measuring gas flow channel L3 is connected to the measuring device 13 that is different from the gas sensor 4. Then at a time of measurement, a part of the exhaust gas G passing the filter F passes the cleaning gas piping 11 and the internal flow channels 51b, 52b, and then is introduced into the measuring device 13 so that the exhaust gas G is measured by the measuring device 13. At this time, it is possible to conduct the comparison measurement to check the sensitivity deterioration of the gas sensor 4 and also possible to measure an item different from an item that can be measured by the gas sensor 4.

In addition, at a time of calibration, with a procedure that a part of the calibration gas supplied to the fixing element 52 passes the internal flow channels 51b, 52b and the cleaning gas piping 11 and then is introduced into the measuring device 13, it is also possible to check gas leakage in the sensor holder 5 by comparing a given component concentration of the calibration gas with a measurement result by the measuring device 13. At this time, since the cleaning and measuring gas flow channel L3 opens continuously to the guide groove 8, it is possible to introduce the calibration gas from the calibration gas flow channel L1 into the cleaning and measuring gas flow channel L3 effectively.

<Regarding Assembling Method and Seal Structure>

A method for assembling the probe unit 2 will be explained with reference to FIG. 4.

First, the filter F is fixed to near the distal end side opening (opening part 502) of the hollow part 521 of the fixing element 52 through a seal member 14 such as graphite fiber packing by means of a fixing member 15. The fixing member 15 of this embodiment is of a cap type and fixes the filter F to the fixing element 52 by being threadably mounted on a screw part, not shown in drawings, formed on the fixing element 52.

Meanwhile, the seal member 16 such as the graphite fiber packing and a sensor fixing plate 17 are inserted in this order into a screw part 4b formed behind the gas introduction bores 4a on the outer circumferential surface of the gas sensor 4, and then a fixing nut 18 is threadably mounted on the screw part 4b. With this procedure, the seal member 16 and the sensor fixing plate 17 are supported between the fixing nut 18 and a sensor nut 19.

Later, the proximal end part of the gas sensor 4 is inserted into the double pipe element 51 and the fixing element 52 is inserted from the distal end side of the gas sensor 4 so that each connecting pipe 522, 523 of the fixing member 52 is fittingly inserted into each internal flow channel 51a, 51b of the double pipe element 51. Then the double pipe element 51 and the fixing element 52 are fastened by a fixing screw (not shown in drawings). With this procedure, the seal member 16 and the sensor fixing plate 17 are supported between the double pipe element 51 and the fixing element 52 so that the probe unit 2 is assembled. At this time, the seal member 16 mounted on the gas sensor 4 locates between the double pipe element 51 and the fixing element 52. With this arrangement, a portion from which the gas might leak locates only on a side of the double pipe element 51. Even for a time of gas leakage, the portion is sealed by the seal member 16 locating between the double pipe element 51 and the fixing element 52. As a result, it is possible to prevent gas leakage with a little amount of the seal member, thereby enabling cost-reduction, structure simplification and facilitation of assembling procedures.

Figure 4:
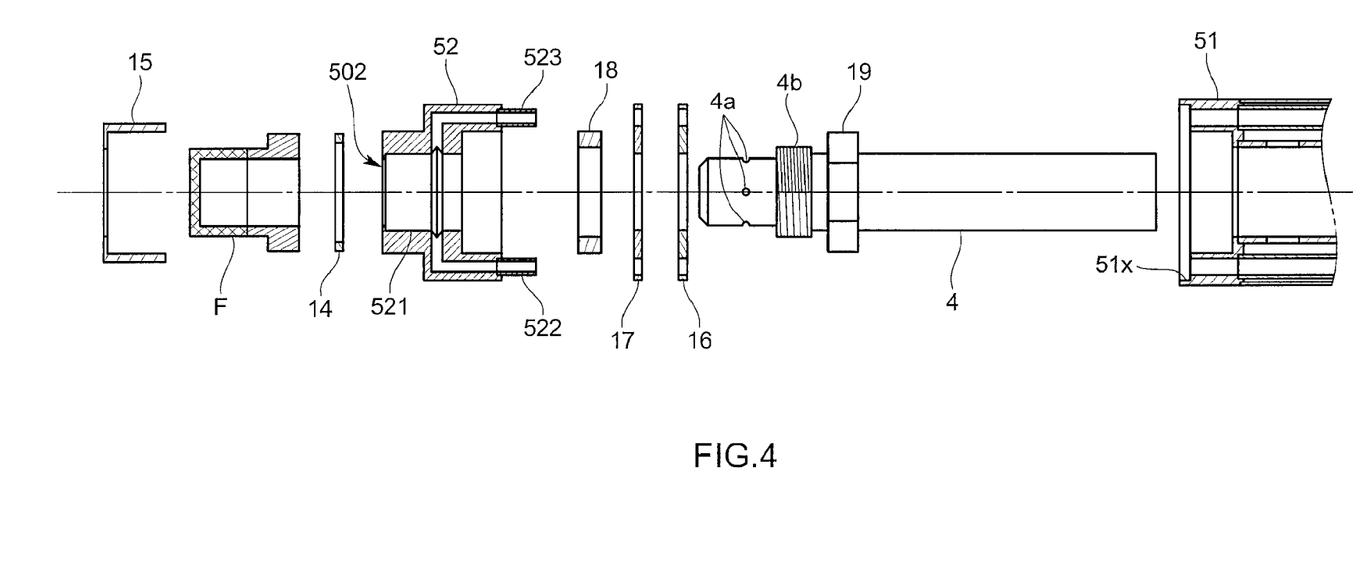
FIG. 4 is an exploded cross-sectional view of the probe unit of this embodiment.

In addition, as shown in a partially magnified view in FIG. 3 and FIG. 4, a concave part 51x to house at least the seal member 16 is formed on a distal end wall front surface of the double pipe element 51. Furthermore, the seal member 16 is housed in the concave part 51x so as not to directly contact the exhaust gas in the duct in a state that the double pipe element 51 is fastened with the fixing member 52. With this arrangement, it is possible to prevent the seal member 16 from being eroded by the exhaust gas.

<Effect of this Embodiment>

In accordance with the exhaust gas analyzer 100 in accordance with this embodiment having the above-mentioned arrangement, in spite of a simple arrangement that the guide groove 8 is arranged on the inner surface 521a of the hollow part 521 surrounding the gas introduction bores 4a along the arranging direction of the multiple gas introduction bores 4a, the calibration gas supplied from the calibration gas flow channel L1 flows along the guide groove 8. As a result, it is possible to make the calibration gas difficult to be affected by a pressure in the duct, especially by a negative pressure in the duct and it is possible to pervade the calibration gas over all of the multiple gas introduction bores 4a without increasing a consumption amount of the calibration gas. In addition, since the guide groove 8 continuous to the opening of the calibration gas flow channel L1 is arranged along the arranging direction of the multiple gas introduction bores 4a, it is possible to introduce the calibration gas into the gas introduction bores 4a irrespective of a positional relationship between the opening of the calibration gas flow channel L1 and the gas introduction bores 4a, which makes it possible to mount the gas sensor 4 on the sensor holder 5 with ease.

<Other Modified Embodiment>

The present claimed invention is not limited to the above-mentioned embodiment.

For example, in the above-mentioned embodiment, the sensor holder 5 is of a double pipe structure and a calibration gas piping 7 forming the calibration gas flow channel L1 is arranged between the inner pipe 511 and the outer pipe 512 forming the double pipe structure, however, the sensor holder 5 may not be of a double pipe structure.

Figure 5:
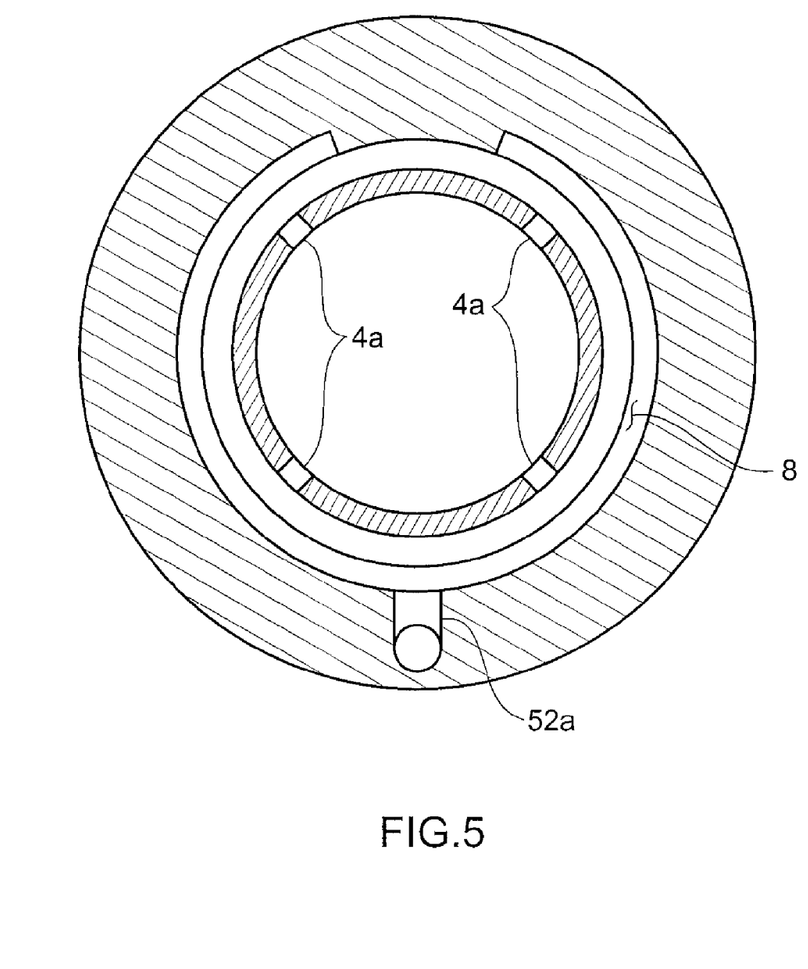
FIG. 5 is a cross-sectional view orthogonal to the axial direction showing a pattern diagram of a guide groove in accordance with a modified embodiment.

In addition, the guide groove 8 in the above-mentioned embodiment is formed to surround the entire circumference of the inner surface 521a of the hollow part 521, however, it may be any as long as it is continuous to the multiple gas introduction bores 4a, and, for example, as shown in FIG. 5, the guide groove 8 may extend from the opening locating on the downstream side of the calibration gas flow channel L1 to both sides in the circumferential direction and may not be continuous at an opposite side of the opening locating at the downstream side.

Figure 6:
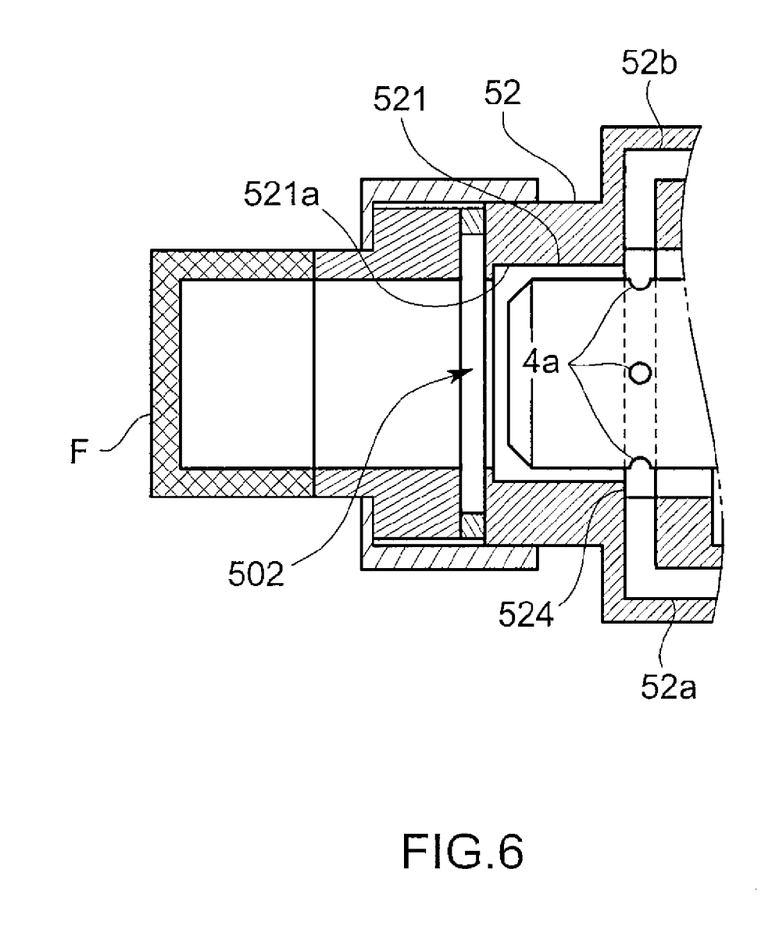
FIG. 6 is a cross-sectional view in the axial direction showing a pattern diagram of a guide groove in accordance with another modified embodiment.

In addition to the above-mentioned embodiment, as shown in FIG. 6, the guide groove may be formed by a step part 524 forming a side surface at an opening on the duct side of the calibration duct channel L1. The step part 524 is arranged along the arranging direction of the gas introduction bores 4a so as to face the gas introduction bores 4a. With this arrangement, a gap between the outer circumferential surface of the gas sensor 4 and the inner surface 521a of the hollow part 521 on a proximal end side from the opening of the calibration gas flow channel L1 becomes bigger than the gap on a distal end side from the opening of the calibration gas flow channel L1.

As a result, even though the pressure in the duct is a negative pressure, it is possible to make the calibration gas difficult to be pulled toward the duct side.

Furthermore, the through bore 501*h* to which the other end of the exhaust pipe in the above-mentioned embodiment is connected is formed on the flange part 501, however, it may be formed on the exhaust pipe. In this case, similar to the above-mentioned embodiment, it is preferable that the through bore 501*h* is formed in the downstream side of the duct from the probe unit 2.

In addition, the present claimed invention is not limited to the above-mentioned embodiment, and it is a matter of course that it may be variously modified without departing from a spirit of the invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A probe unit for taking a sample of an exhaust gas flowing in a duct, the probe unit comprising:
    a gas sensor having an inside, and having multiple gas introduction bores for introducing a gas into the inside of the gas sensor;
    a sensor holder inside of which the gas sensor is held and that is arranged to be inserted inside of the duct so as to introduce the exhaust gas flowing in the duct into the gas sensor;
    a calibration gas flow channel that is arranged in the sensor holder and that has an opening at an inner surface of a side wall, surrounding the gas introduction bores of the gas sensor, of the sensor holder so as to supply a calibration gas to the gas sensor; and
    a guide groove that is arranged continuous to the opening of the calibration gas flow channel and arranged on the inner surface of the side wall along an arranging direction of the multiple gas introduction bores to face the multiple gas introduction bores.

2. An exhaust gas analyzer using the probe unit of claim 1.

3. The probe unit of claim 1 wherein the guide groove is formed to surround an entire circumference of the inner surface of the side wall.

4. An exhaust gas analyzer using the probe unit of claim 3.

5. The probe unit of claim 1 wherein the calibration gas flow channel supplies the calibration gas to the gas sensor by speeding up a flow rate of the calibration gas by narrowing a flow channel on the opening side of the calibration gas flow channel.

6. An exhaust gas analyzer using the probe unit of claim 5.

* * * * *